United States Patent [19]

Guettler et al.

[11] Patent Number: 5,573,931
[45] Date of Patent: Nov. 12, 1996

[54] METHOD FOR MAKING SUCCINIC ACID, BACTERIAL VARIANTS FOR USE IN THE PROCESS, AND METHODS FOR OBTAINING VARIANTS

[75] Inventors: Michael V. Guettler, Holt; Mahendra K. Jain, Okemos; Denise Rumler, Leslie, all of Mich.

[73] Assignee: Michigan Biotechnology Institute, Lansing, Mich.

[21] Appl. No.: 520,348

[22] Filed: Aug. 28, 1995

[51] Int. Cl.$^6$ .................................. C12P 7/46; C12P 1/04
[52] U.S. Cl. ...................... 435/145; 435/170; 435/252.1; 435/822
[58] Field of Search ................................. 435/145, 252.1, 435/170, 822

[56] References Cited

U.S. PATENT DOCUMENTS 5,143,834  9/1992  Glassner et al. .......................... 435/145
5,168,055  12/1992  Datta et al. .............................. 435/145

*Primary Examiner*—Herbert J. Lilling
*Attorney, Agent, or Firm*—Quarles & Brady

[57] ABSTRACT

A method for producing succinic acid in high concentration by fermentation employs a variant of strain 130Z which is resistant to concentrations of about 1 g/l to about 8 g/l of sodium monofluoroacetate. The variant produces succinic acid in concentrations of about 80 g/l to about 110 g/l and the fermentation product contains less formic and acetic acids than the product obtained using the parent strain under identical conditions. The novel variants and a method of obtaining such variants also are described.

6 Claims, No Drawings

METHOD FOR MAKING SUCCINIC ACID, BACTERIAL VARIANTS FOR USE IN THE PROCESS, AND METHODS FOR OBTAINING VARIANTS

FIELD OF THE INVENTION

This invention relates to a method for making succinic acid, variants of succinic acid producing organisms, and methods for obtaining such variants. The variants produce higher concentrations of succinic acid with higher yields and improved productivity as compared to the parent strain.

BACKGROUND OF THE INVENTION

Succinic acid and its derivatives are widely used as specialty chemicals for applications in foods, pharmaceuticals, and cosmetics.

The Glassner et al U.S. Pat. No. 5,143,834 and the Datta et al U.S. Pat. Nos. 5,168,055, both disclose integrated processes for the production of succinic acid. These patents employed the anaerobic bacterium *Anaerobiospirillum succiniciproducens* (ANS) which produces comparatively low concentrations of succinic acid, approximately 35 g/l. However, commercial fermentations which are used for the bulk production of organic acids, such as citric and lactic acids, typically produce higher concentrations of acids, e.g. 80-120 g/l. Likewise, the production of high concentrations of succinic acid is needed for an economical commercial production of succinic acid.

The accumulation of very high concentrations of acids in a fermentation broth is not a normal phenomenon for microorganisms and thus the development of a commercial fermentation process usually depends on improvement of naturally occurring strains. Strain selection and strain mutation are techniques frequently used to obtain improved strains that produce high yields of organic acids. However, finding improved strains is a very difficult process, and without methods that favor and identify high producing strains it is normally necessary to examine as many as 100,000–1,000,000 clones to find even one improved strain.[1]

It would be advantageous to have a fermentation method for producing the higher concentrations of succinic acid which are necessary for commercial production. It also would be advantageous to have microorganisms that produce higher concentrations of succinic acid and methods of selecting those microorganisms.

SUMMARY OF THE INVENTION

It is an object of the present invention to disclose a fermentation method of producing succinic acid in the high concentrations necessary for commercial production.

It also is an object to disclose microorganisms that produce high concentrations of succinic acid.

It is a further object of the present invention to disclose a method for obtaining microorganisms that produce high levels of succinic acids.

The method of the present invention for making succinic acid comprises providing an aqueous fermentation medium containing a culture of a microorganism and a source of fermentable carbon; cultivating said microorganism under anaerobic conditions in the presence of carbon dioxide to form succinic acid in a concentration of about 80 g/l to about 110 g/l in the fermentation medium.

The novel microorganisms for use in the above method are variants of a parent strain 130Z which are more resistant to fluoroacetate than the parent. The variants produce more succinic acid and less formic and acetic acid in the fermentation method than a corresponding fermentation using the parent strain under otherwise identical conditions. The fermentation product obtained can have a succinic/acetic ratio of as high as 85 and a succinic/formic ratio of 160. Because the concentrations of formic and acetic acids are lower the succinic acid can be more readily recovered and purified by electrodialysis.

The method of the present invention for obtaining the novel variants of strain 130Z which upon fermentation produces higher levels of succinic acid and lower levels of formic and acetic acids than the parent organism, comprises growing strain 130Z upon plates of a nutrient medium containing fermentable carbon and about 1.0 g/l to about 8 g/l of pure clones of the variants which are resistant to the sodium monofluoroacetate and isolating biologically monofluoroacetate and which produce high levels of succinic acid and low levels of formic and acetic acids.

The described method of the present invention for obtaining the desired variants uses monofluoroacetate ions at concentrations that prevent the growth of the vast majority (e.g. 100,000–1,000,000 or more clones) of a parent strain of a succinic acid producing bacteria, but which allows for the normal growth of a few resistant variants that are markedly improved in their ability to produce succinic acid. These new variants produce higher concentrations of succinic acid, at a higher rate, and with an improved yield as compared to their parent strain under identical conditions. This novel selection and screening method does not use genome disruptive non-directed mutagens or recombinant DNA methods.

Although how the method works is not completely understood, it is clear that the new high producing variants produce reduced amounts of formic and acetic acid as compared to their parent strain. It has been noted that the accumulation of acetate and formate in the fermentation broth contributes to the cessation of growth and fermentation by the producing organism, and the effect is particularly pronounced at a low external pH's.[2,3] It is believed that the reduction in acetate and formate accumulation in the fermentation broth in the practice of the method of the present invention possibly extends the biocatalytic life of the succinic acid producing biomass. It also is known that it is necessary to increase the amount of carbon flow in the succinate specific pathway to increase the succinate yield. Therefore, by using the novel variants of the present invention additional carbon may be diverted to producing succinate as opposed to producing acetate and formate.

In a preferred practice of the method, we have obtained biologically pure cultures of variants that are more resistant to fluoroacetate than their parent and that can produce more than 100 g/l succinic acid in 48 hours. The preferred fluoroacetate resistant variants can produce succinic acid with yields as high as 97% based on the weight of the dextrose consumed.

The preferred parent strain is strain 130Z which is a Gram negative rod that produces 75 g/l succinic acid in 48 hours with a 77% weight yield. Strain 130Z was isolated from bovine rumen contents at the Michigan Biotechnology Institute in Lansing, Mich. It has been deposited with the American Type Culture Collection of Rockville, Md., USA as a Budapest Treaty deposit (ATCC No. 55618).

DESCRIPTION OF THE PREFERRED EMBODIMENTS OF THE INVENTION

In the preferred embodiment of the method of the present invention for producing succinic acid the succinic acid producing bacteria employed are variants which were derived from strain 130Z (ATCC 55618).

In the preferred method of obtaining the variants, the strain 130Z is grown in a culture containing fermentable carbon and other required nutrients and a sodium monofluoroacetate concentration of about 1 g/l to about 8 g/l at about 37° C. in a 100% $CO_2$ atmosphere for about 7 to 10 days to obtain biologically pure cultures of the variants.

The practice of the invention is further illustrated by the Examples in which the media, fermentations and analytical procedures were the following:

MEDIA:

Defined medium contained NaCl, 0.58 g; $K_2SO_4$, 0.10 g; $MgCl_2.6H_2O$, 0.02 g; $CaCl_2$, 0.002 g; $K_2HPO_4$, 3.5 g; $KHPO_4$, 2.7 g; monosodium glutamate, 1.5 g; Bacto yeast extract, 0.1 g; $B_{12}$, 10µg; biotin, folic acid, 200µg; thiamine, riboflavin, niacin, pantothenate, p-aminobenzoate, and lipoic acid, 500 µg; $B_6$, 1 mg; and dextrose, 100 g per liter. The liquid medium contained $MgCO_3$, 1.0 g per liter. Plates contained Bacto agar, 15 g and $MgCO_3$, 8 g per liter.

Complex medium contained corn steep liquor (Solulys L 48B, Roquette Inc. Gurnee, IL), 10–15 g; Bacto yeast extract, 5–15 g; $NaH_2PO_4.H_2O$, 1.16 g; $Na_2HPO_4$, 0.31 g; NaCl, 1.0 g; $MgCl_2.6H_2O$, 0.2 g; $CaCl_2.2H_2O$, 0.2 g; $B_{12}$, 10µg; biotin, folic acid, 200 µg; thiamine, riboflavin, niacin, pantothenate, p-aminobenzoate, and lipoic acid, 500 µg; $B_6$, 1 µg; $MgCO_3$, 80 g; sodium acetate, 1.5–3.5 g; dextrose, 100–135 g per liter.

Corn fiber hydrolysate (CFH) medium contained CFH, 760 ml; yeast extract, 10 g; $NaH_2PO_4.H_2O$ 1.16 g; $Na_2HPO_4$ 0.31 g; d-biotin, 10 µg per liter. The CFH was prepared from corn fiber (Cargill Inc., Wayzata, Minn.) that was pretreated with 0.5% $H_2SO_4$ and hydrolysed with 15 U per gram of cellulase (Cytolase 300, Genencor, Rochester, N.Y.) and β-glucosidase (Novo 188, Novo Nordisk, Danbury, Conn.). The CFH, phosphates, yeast extract, and biotin were sterilized separately and combined in vials containing 0.8 g $MgCO_3$.

Peptone yeast glucose (PYG) medium was prepared as described in the VPI manual (Holdemann 1977) and was dispensed into tubes with serum vial butyl rubber closures (Belco Glass) 10 ml per tube. A phosphate buffer was added after autoclaving, $KH_2PO_4$, 1.5 g; $K_2HPO_4$, 2.9 g per liter.

ANALYSIS:

The organic acid fermentation products were analyzed using high-performance liquid chromatography (HPLC).[4] Organic acids were analyzed chromatographically by elution with 0.006 N $H_2SO_4$ from a cation exchange resin in the hydrogen form. A Waters Model 600 HPLC system with a Bio-Rad HPX-87H column and a Waters Model 410 Refractive Index detector were used in this analysis. Dextrose concentrations were also determined by this HPLC method. Arabinose and xylose were determined with the same HPLC instruments but using an Interaction CHO682 lead column with deionized water as the mobile phase.

FERMENTATIONS:

Vial Fermentations: Serum vials containing $MgCO_3$ and 10 ml of liquid culture were used for vial experiments. The vials were prepared by adding 0.8 grams of $MgCO_3$ and 5 ml of double strength complex medium to each serum vial (58 ml Belco Glass). The vials were flushed with $CO_2$, closed with rubber stoppers and autoclaved for 15 minutes at 121° C. and 15–20 psi. The dextrose, phosphate, and vitamins were added by sterile syringe from concentrated sterile solutions after autoclaving. A 24 hour inoculum was raised in the same medium and the addition of 0.5 ml of inoculum brought the total liquid volume to 10 ml. For the biomass fermentation the inoculum was raised with glucose and xylose for approximately 24 hours. The 10% inoculum used brought the total culture volume to 10 ml. The vials were gassed with $CO_2$ and charged to 5 psi. Incubation was at 37° C. on a New Brunswick Gyrotatory Shaker Model G25 (New Brunswick Scientific, Edison, N.J.).

Small scale fermentations: They were done with 1 liter of complex medium in 2 liter MultiGen fermenters (New Brunswick Scientific, Edision, N.J.). They were autoclaved for 35 minutes at 122° C. and 15–20 psi. The temperature was controlled at 39° C. Carbon dioxide was sparged at 0.05–0.1 volume/volume/minute. The culture was stirred at 600 rpm with two flat six-blade Rushton impellers. An actively growing inoculum was raised in rubber stoppered serum vials containing the complex medium and 40–80 g/l $MgCO_3$. A 5% percent inoculum was used.

For succinic acid production using $Na^+$ instead of $Mg^{++}$ the pH was automatically controlled with the addition of 10 N NaOH, or a 7N combination of NaOH (1.5 M) and $Na_2CO_3$ (2.75M). For succinic acid production using $NH_4^+$ instead of $Mg^{++}$ the pH was automatically controlled with the addition of 4–10 N $NH_4$ OH. The pH was automatically controlled at 6.6–6.8 with a Cole Parmer Controller model 5997–30 and Imatic pump (Cole Parmer, Chicago, Ill.).

EXAMPLE 1

Isolation of Variants that Produce High Concentrations of Succinic Acid

A biologically pure culture of 130Z (ATCC 55618) was grown overnight using the above defined medium plus casamino acids (1.8 g/l). One ml of the overnight culture was diluted with 10 ml fresh defined medium and 0.1 ml aliquots of the thus diluted culture were spread onto plates containing 2–8 mg/ml fluoroacetate. Incubation was at 37° C. in a 100% $CO_2$ atmosphere. Colonies developed on these plates in about 7–10 days. Single well isolated colonies of variants were picked and restreaked on individual sectors of fresh fluoroacetate plates. These individual resistant clones were grown for 3–7 days under the same conditions. Biologically pure cells from each clone were picked with a sterile 22G needle and washed into tubes of PYG medium. The fluoroacetate resistant clones were grown in the PYG medium for 18–24 hours and their products were determined by HPLC. The variants that produced reduced amounts of acetic and formic acid were retained for evaluation as to their ability to produce succinic acid using the complex medium in both small vial and in 1 liter fermentations.

EXAMPLE 2

Vial Fermentations Using the Variants and Strain 130Z

The variants employed were made by the process of Example 1 and selected without the use of any mutagens to avoid obtaining strains with undesirable secondary mutations. Approximately 8–10% of the fluoro-resistant isolates accumulated several grams of pyruvic acid and produced reduced amounts of acetic acid and formic acid from dextrose when grown in the PYG screening medium, while other fluoroacetate resistant isolates produced the same profile of metabolic endproducts as the 130Z parent. The metabolic products produced by five variants of the pyruvic acid accumulating type are given in Table 1 along with the products produced by the parent strain 130Z. Variants FZ 6, FZ 9, FZ 21, FZ 45, and FZ 53 were typical of the pyruvic acid accumulating fluoroacetate resistant strains. They produced different product profiles, but their morphology and general growth characteristics are similar to the 130Z parent. These variants are spontaneous physiologic mutants preferentially selected by the fluoroacetate containing medium and identified by the screening method. The most noteworthy feature of these fluoroacetate resistant variants is their succinic acid productivity and ability to produce and accumulate succinic acid in levels above 90 g/l. There are slight differences among these strains, but all of them produce higher concentrations of succinic acid at a higher rate and with an improved yield as compared to 130Z. They also produce less acetic and formic acid than 130Z.

TABLE 1

Products produced in 10 ml PYG screening medium.

| Strains | Concentration (g/l) | | | |
|---|---|---|---|---|
| | Succinic | Acetic | Formic | Pyruvic |
| 130Z | 3.3 | 2.2 | 1.6 | 0.2 |
| FZ 6 | 3.9 | 0.1 | 0.0 | 3.1 |
| FZ 9 | 3.4 | 0.1 | 0.0 | 2.8 |
| FZ 21 | 3.3 | 0.3 | 0.1 | 2.6 |
| FZ 45 | 3.8 | 0.2 | 0.0 | 2.8 |
| FZ 53 | 4.5 | 0.5 | 0.2 | 2.7 |

Strain 130Z typically produced about 68–78 g/l of succinic acid in 10 ml shake vial cultures using the complex medium. However, it also produced relatively high amounts of acetic and formic acid. The fluoroacetate resistant variants of strain 130Z outperformed the parent and produced succinic acid concentrations approaching or exceeding 100 g/l under all nutrient conditions. They also produced less acetic and formic acid than 130Z (Tables 2, 3, and 4). The variants produced succinic concentration 26–41% higher than the 130Z strain under low nutrient conditions (Table 2). The variants produced succinic concentration 12–27% higher than the parent strain under high nutrient conditions (Table 4). In addition, the variants, such as FZ 6 and FZ 21, produced about 10% more succinic acid yield than 130Z under all nutrient conditions (Tables 2, 3, 4).

TABLE 2

Vial fermentations with low nutrient conditions.
(Corn steep 10 g/l; yeast extract 5 g/l.)

| | Concentration (g/l) | | | | | % |
|---|---|---|---|---|---|---|
| | Succinic | Acetic | Formic | Pyruvic | Propionic | yield* |
| 130Z | 68.5 | 15.1 | 3.9 | 9.8 | 0.9 | 85 |
| FZ 6 | 86.9 | 4.9 | 0.0 | 12.5 | 0.7 | 94 |
| FZ 21 | 96.4 | 16.5 | 0.0 | 4.4 | 3.6 | 89 |

*% yield = (grams succinic acid/grams dextrose) × 100.

TABLE 3

Vial fermentations with medium nutrient conditions.
(Corn steep 15 g/l; yeast extract 5 g/l.)

| | Concentration (g/l) | | | | | % |
|---|---|---|---|---|---|---|
| | Succinic | Acetic | Formic | Pyruvic | Propionic | yield* |
| 130Z | 69.4 | 14.9 | 3.7 | 8.9 | 1.1 | 84 |
| FZ 6 | 95.9 | 7.1 | 0.0 | 14.8 | 0.8 | 97 |
| FZ 21 | 96.2 | 10.2 | 0.0 | 3.0 | 2.5 | 87 |

TABLE 4

Vial fermentations with high nutrient conditions.
(Corn steep 10 g/l; yeast extract 15 g/l.)

| | Concentration (g/l) | | | | | % |
|---|---|---|---|---|---|---|
| | Succinic | Acetic | Formic | Pyruvic | Propionic | yield* |
| 130Z | 79.8 | 21.4 | 10.4 | 7.5 | 2.6 | 82 |
| FZ 6 | 92.1 | 5.2 | 0.0 | 15.4 | 1.4 | 82 |
| FZ 21 | 101.0 | 16.4 | 0.0 | 3.4 | 3.3 | 92 |

Succinic acid production by 130Z is tractable by nutrient manipulation and responsive to optimization efforts. The rate and extent of its growth was markedly influenced by the addition of yeast extract. Yeast extract increased the rate of fermentation and the succinic acid concentration. Corn steep liquor (CSL) has the effect of improving succinic acid yields. Therefore, nutrient sources can be combined to provide a high fermentation rate, high concentration, and high yield; optimum combinations can be arrived at empirically and adjusted to obtain the best economic results. The fluoroacetate resistant variants of 130Z have retained this property. In Table 5, it is seen that triplicate vials of FZ 6 produced an average of 93 g/l of succinic acid with an average yield of 94%. With the lower nutrient condition the succinic acid yield was increased by 10–12% and more succinic acid was produced with 10 g/l less yeast extract.

TABLE 5

FZ 6 succinic acid yield.

| Nutrient level | Concentration (g/l) | | | average succinic yield (wt %) |
|---|---|---|---|---|
| | CSL | Yeast extract | average succinic acid | |
| low | 10 | 5 | 84.9 | 92 |
| medium | 15 | 5 | 93.4 | 94 |
| high | 10 | 15 | 90.4 | 82 |

EXAMPLE 3

Fermentations at 1-liter Using Variants and Parent Strain 130Z

The parent strain 130Z produced succinic acid as a major product and produced concentrations of succinic acid higher than any other previously described strain. The results from a fermentation using Bacterium 130Z are given in Table 6 for comparison with fermentations using the variants. All the fermentations were done with the minimum of modern sophistication to emphasize the ability of these strains to produce very high concentrations of succinic acid with a minimum of refinement. However, it is recognized that controlling or programming certain fermentation parameters near their optima is likely to result in improved production.

Automatic pH control was not used in this fermentation. The pH was allowed to drop during the course of the fermentation. The pH decline was moderated by the presence of 80 grams of $MgCO_3$ that was added to the fermenter prior to autoclaving.

Strain 130Z produced 61 g/l in 34 hours and a final concentration of 67 g/l. Strain 130Z typically produces 65–78g/l of succinic acid when it is grown in a 1-liter fermenter with 15 g/l of yeast extract, corn steep liquor, and sufficient glucose. The succinic acid yield is usually about 70% under these high nutrient conditions.

TABLE 6

130Z fermentation.

| | Concentration (g/l) | | | | | |
|---|---|---|---|---|---|---|
| Time | Dextrose | Succinic | Acetic | Formic | Propionic | Pyruvic | pH |
| 0 | 101.4 | 0.8 | 0.4 | 0.2 | 0.4 | 0.0 | 7.0 |
| 8.5 | 70.1 | 17.6 | 8.3 | 6.8 | 0.2 | 0.0 | 6.8 |
| 12 | 53.8 | 29.4 | 9.7 | 8.1 | 0.5 | 0.0 | 6.6 |
| 15 | 41.5 | 38.6 | 10.4 | 8.4 | 0.5 | 4.6 | 6.4 |
| 18 | 31.3 | 45.9 | 10.6 | 8.1 | 0.5 | 4.8 | 6.4 |
| 23 | 21.9 | 53.2 | 11.1 | 8.3 | 0.7 | 5.0 | 6.3 |
| 34.25 | 11.4 | 61.1 | 11.8 | 8.3 | 1.1 | 4.9 | 6.3 |
| 41 | 8.6 | 62.3 | 11.7 | 8.2 | 1.4 | 4.3 | 6.3 |
| 58.25 | 5.8 | 65.0 | 11.8 | 8.1 | 1.9 | 4.8 | 6.2 |
| 84 | 3.1 | 67.2 | 12.0 | 8.7 | 2.5 | 4.3 | 6.2 |

As seen in Table 7 the variant FZ 21 produced 80.7 g/l of succinic acid in 35 hours, an improvement of 32% over parent 130Z. Automatic pH control was not used but pH decline was moderated by the presence of 80 grams of $MgCO_3$. The succinic acid yield was 78%.

TABLE 7

FZ 21 fermentation.

| | Concentration (g/l) | | | | | |
|---|---|---|---|---|---|---|
| Time | Dextrose | Succinic | Acetic | Formic | Propionic | Pyruvic | pH |
| 0 | 114.1 | 4.4 | 3.1 | 0.0 | 0.0 | 0.6 | 7.05 |
| 21.25 | 47.3 | 53.4 | 8.8 | 0.4 | 0.0 | 0.0 | 6.60 |
| 26.25 | 30.0 | 66.7 | 9.7 | 0.5 | 0.0 | 0.0 | 6.40 |
| 30.75 | 18.2 | 76.3 | 8.4 | 0.4 | 0.0 | 0.0 | 6.10 |
| 35.25 | 11.6 | 80.7 | 10.7 | 0.3 | 0.0 | 0.3 | 5.97 |
| 47 | 8.8 | 81.9 | 10.3 | 0.0 | 2.0 | 3.2 | 6.05 |

As seen in Table 8 variant FZ 53 produced over 94 g/l in 34.25 hours an improvement of 54% over the parent 130Z. A total of 95 grams of $MgCO_3$ was used in this fermentation. After 25 hours 15 grams of sterilized $MgCO_3$ was added through the head plate, supplementing the 80 grams of $MgCO_3$ that was added to the fermenter prior to autoclaving. The succinic acid yield with this fermentation was 78%.

TABLE 8

FZ 53 fermentation with insufficient pH control.

| | Concentration (g/l) | | | | | |
|---|---|---|---|---|---|---|
| Time | Dextrose | Succinic | Acetic | Formic | Propionic | Pyruvic | pH |
| 0 | 129.2 | 1.8 | 2.6 | 0.0 | 0.0 | 1.0 | |
| 10.25 | 105.4 | 20.1 | 5.9 | 0.2 | 0.0 | 0.0 | 6.90 |
| 24.5 | 30.2 | 76.8 | 9.6 | 0.5 | 0.0 | 0.0 | 6.14 |
| 34.25 | 8.6 | 94.4 | 11.7 | 0.4 | 0.0 | 0.6 | 5.85 |
| 37.75 | 7.1 | 95.4 | 14.4 | 0.4 | 0.0 | 0.3 | 5.88 |
| 42.25 | 6.8 | 95.5 | 13.7 | 0.4 | 1.4 | 0.6 | 5.82 |
| 48 | 6.6 | 96.5 | 13.8 | 0.6 | 1.7 | 0.4 | 5.89 |
| 59.75 | 6.5 | 96.2 | 11.8 | 0.6 | 2.2 | 0.3 | 5.92 |

As seen in Table 9 with the pH sufficiently controlled FZ 53 produced 105 g/l succinic acid as a final concentration, 30% higher than the highest concentration ever achieved by bacterium 130Z. The succinic acid yield was 83%. Supplemental pH maintenance was shown to be important to maintain a high rate of biocatalytic activity and for the production of higher concentrations in the fermenter. A total of 95 grams of $MgCO_3$ was used. After 35 hours, 15 grams of sterilized $MgCO_3$ was added through the head plate, supplementing the 80 grams that was added prior to autoclaving. The pH was maintained at or above 6.0 through the addition of approximately 1 gram of $Mg(OH)_2$ at 41 hours and again at 52 hours.

TABLE 9

FZ 53 fermentation with additional pH control.

| | Concentration (g/l) | | | | | |
|---|---|---|---|---|---|---|
| Time | Dextrose | Succinic | Acetic | Formic | Propionic | Pyruvic | pH |
| 0 | 132.8 | 1.2 | 2.4 | 0.0 | 0.0 | 0.0 | 7.20 |
| 6.25 | 123.6 | 7.8 | 3.5 | 0.0 | 0.0 | 1.6 | 6.90 |
| 13 | 99.9 | 26.4 | 6.6 | 0.4 | 0.1 | 1.6 | 6.70 |
| 20.5 | 66.4 | 51.7 | 9.4 | 0.7 | 0.3 | 3.1 | 6.55 |
| 29.25 | 39.0 | 75.1 | 11.2 | 0.6 | 1.1 | 3.3 | 6.30 |
| 35.5 | 28.2 | 85.1 | 15.3 | 0.7 | 1.1 | 3.2 | 6.00 |
| 41.75 | 17.2 | 93.7 | 16.2 | 0.6 | 1.6 | 2.6 | 6.22 |
| 52.25 | 7.4 | 103.4 | 17.6 | 0.7 | 1.8 | 2.4 | 6.05 |
| 78 | 4.4 | 105.8 | 18.1 | 0.7 | 1.9 | 2.3 | 6.08 |

EXAMPLE 4

Succinic acid production using automatic pH control

Automatic pH control can be used to neutralize the succinic acid produced by 130Z and its derivatives. Suspensions of $Mg(OH)_2$ can be used with a pump and pH controller to replace part or all of the $MgCO_3$ added to the succinic acid fermentations for pH maintenance. Basic solutions containing cations other than $Mg^{++}$ can also be added automatically to neutralize the succinic acid. For example: $NH_4OH$, $NaOH$, or $Na_2CO_3$ solutions can be used to neutralize succinic acid produced during fermentation. The fluoroacetate resistant strain FZ 6 performed better than the parent strain in fermentations using the sodium or ammonium cations (Table 10 & 11). These results demonstrate that the fluoroacetate resistant derivatives of Strain 130Z produce high concentrations of succinic acid in a fermentative process that can be neutralized with a variety of alkali.

TABLE 10

Succinic acid production using ammonium hydroxide.

| Strain | Time (hr) | Succinic (g/l) | Strain | Time (hr) | Succinic (g/l) |
|---|---|---|---|---|---|
| 130Z | 49 | 29.3 | FZ 6 | 46.3 | 54.6 |
|  | 86 | 29.8 |  | 62.8 | 63.7 |

TABLE 11

Succinic acid production using sodium alkali.

| Strain | Time (hr) | Succinic (g/l) | Strain | Time (hr) | Succinic (g/l) |
|---|---|---|---|---|---|
| 130Z | 49 | 51.9 | FZ 6 | 44.3 | 56.9 |
|  | 86 | 53.6 |  | 64 | 63.2 |

EXAMPLE 5

Succinic acid from other substrates

A number of other substrates such as sucrose, xylose, and arabinose can be used by the fluoroacetate resistant strains of bacterium 130Z to produce succinic acid. These strains can also utilize the sugar present in by-products and refinery waste streams such as molasses and raffinate. Fluoroacetate resistant strains can also utilize the sugar produced from the enzymatic hydrolysis of biomass. These strains utilize dextrose, xylose, and arabinose simultaneously and produce succinic acid.

Strain FZ 6 produced 70.6 g/l of succinic acid from corn fiber hydrolysate (CFH) that contained dextrose, xylose, and arabinose with an 88% yield based on weight of the three sugars consumed (Table 12). The biomass hydrolysate also replaced the corn steep liquor (CSL) which is normally present in the medium.

TABLE 12

FZ 6 Vial fermentations using corn fiber hydrolysate.

| Time (hr) | Succinic | Formic | Acetic | Propionic | Dextrose | Xylose | Arabinose | % yield |
|---|---|---|---|---|---|---|---|---|
| 0.0 | 5.4 | 0.0 | 0.1 | 0.0 | 61.1 | 8.2 | 9.6 |  |
| 24 | 55.6 | 0.0 | 3.3 | 0.0 | 12.5 | 1.3 | 0.2 | 77 |
| 101 | 70.6 | 0.3 | 2.8 | 3.0 | 2.4 | 1.4 | 0.9 | 88 |

It will be apparent to those skilled in the art that a number of changes and modifications can be made without departing from the spirit and scope of the invention. Therefore, it is intended that the invention only be limited by the claims.

References

1. Mattey, M. (1992). The production of organic acids. Crit. Rev. Biotechnol. 12:87–132.
2. Baronofsky J. J., W. J. A Schreurs, and E. R. Kashket. (1984). Uncoupling by acetic acid limits growth and acetogenesis by *Clostridium thermoaceticum*. Appl. Environ. Microbiol. 48: 1134–1139.
3. Linton, J. D., K. Griffiths, and M. Gregory. (1981). The effect of mixtures of glucose and formate on yield and respiration of a chemostat culture of *Beneckea natriegens*. Arch. Microbiol. 129:119–122.
4. Guerrant et al. ( 1982 ). J. Clinical. Microbiol., 16:355.

We claim:

1. In the method of preparing succinic acid by the fermentation of a nutrient medium containing fermentable carbon with a microorganism, the improvement which comprises employing as the microorganism a mutant of strain 130Z (ATCC No. 55618) which produces succinic acid in concentrations of about 80 g/l to about 110 g/l and which is resistant to levels of sodium monofluoroacetate of about 1 g/l to about 8 g//l.

2. A method of producing succinic acid by the fermentation of a carbohydrate containing medium with a microorganism which comprises employing a mutant of strain 13OZ (ATCC No. 55618) which produces succinic acid in concentrations of from about 80 g/l to about 110 g/l and less formic and acetic acids with the succinic acid than the parent strain 130Z of which it is a mutant.

3. A method for the production of succinic acid which comprises providing an aqueous fermentation medium containing a culture of a microorganism and a source of assimilable carbon; cultivating said organism under anaerobic conditions in the presence of carbon dioxide to form succinic acid in a concentration of about 80 g/l to about 110 g/l in said fermentation medium; and wherein said organism is a mutant of strain 130Z, said mutant being resistant to sodium monofluoroacetate concentrations of 1 g/l to about 8 g/l and producing less formic and acetic acids in the fermentation medium than a corresponding fermentation using the parent strain under otherwise identical conditions.

4. A method of obtaining a mutant of strain 130Z which upon fermentation upon a carbohydrate containing medium produces more succinic acid and less formic and acetic acids than its parent organism, said method comprising growing strain 130Z in a nutrient medium containing from 1 g/l to about 8 g/l of sodium monofluoroacetate, isolating colonies of the strain 130Z mutants that are growing from the first container, placing those colonies in a second container containing nutrient medium without monofluoroacetate, incubating said second container, measuring the amount of succinic acid, formic acid, acetic acid and pyruvic acid produced by the colonies of the strain 130Z mutants in said second container, and isolating in the second container the colonies of the strain 130Z mutants which produce higher amounts of succinic acid and lower amounts of formic and acetic acids than the parent strain.

5. An isolated, biologically pure culture of a mutant of strain 130Z (ATCC No. 55618), said mutant being resistant to sodium monofluoroacetate concentrations of about 1 g/l to about 8 g/l and able to produce succinic acid in concentrations of from about 80 g/l to about 110 g/l.

6. A mutant of claim 5 which has the identifying characteristics of strain 130Z (ATCC No. 55618).

* * * * *